US012472026B2

(12) United States Patent
Ramstad et al.

(10) Patent No.: US 12,472,026 B2
(45) Date of Patent: Nov. 18, 2025

(54) MECHANISM FOR MANAGING AND RETAINING A SURGICAL DRAPE

(71) Applicant: INTUITIVE SURGICAL OPERATIONS, INC., Sunnyvale, CA (US)

(72) Inventors: Craig R. Ramstad, Minden, NV (US); Jeffrey R. Roeder, Mountain View, CA (US); Jeffrey D. Brown, Palo Alto, CA (US); Robert E. Holop, Santa Clara, CA (US); Anthony K. McGrogan, San Jose, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 18/545,555

(22) Filed: Dec. 19, 2023

(65) Prior Publication Data

US 2024/0189056 A1 Jun. 13, 2024

Related U.S. Application Data

(62) Division of application No. 16/317,285, filed as application No. PCT/US2017/038350 on Jun. 20, 2017, now Pat. No. 11,883,123.

(Continued)

(51) Int. Cl.
*A61B 46/10* (2016.01)
*A61B 17/00* (2006.01)
*A61B 34/30* (2016.01)

(52) U.S. Cl.
CPC .............. *A61B 46/10* (2016.02); *A61B 34/30* (2016.02); *A61B 2017/00477* (2013.01); *A61B 2034/302* (2016.02)

(58) Field of Classification Search
CPC . A61B 1/00135; A61B 1/00142; A61B 50/00; A61B 2017/00477;

(Continued)

(56) References Cited

U.S. PATENT DOCUMENTS

RE21,753 E 3/1941 Willard et al.
3,483,494 A 12/1969 Harry (Continued)

FOREIGN PATENT DOCUMENTS

BE 853518 A 8/1977
BE 1018961 A4 11/2011

(Continued)

OTHER PUBLICATIONS

KR 20110036452 A translation (Year: 2011).*

(Continued)

*Primary Examiner* — Caitlin A Carreiro
(74) *Attorney, Agent, or Firm* — Jones Robb, PLLC

(57) ABSTRACT

A cinch assembly affixed to a surgical drape may include at least two pairs of links connected by a hinge joint, with each link foldable relative to one another about the hinge joint between an unfolded configuration and a folded configuration. A portion of the surgical drape may be in an extended configuration when the pairs of links are in the unfolded configuration and may be in a gathered configuration when the pairs of links are in the folded configuration. The cinch assembly may further include at least two alignment and attachment element assemblies including first and second attachment elements configured to align with and engage with first and second complementary attachment elements of equipment of a surgical system.

15 Claims, 9 Drawing Sheets

Related U.S. Application Data

(60) Provisional application No. 62/362,194, filed on Jul. 14, 2016.

(58) Field of Classification Search
CPC ... A61B 2034/302; A61B 34/30; A61B 46/00; A61B 46/10; A61B 46/23; A41F 1/00; A41F 19/005; A41F 9/02; A41F 9/025; A41F 18/00; A41F 19/00
USPC ................. 600/119, 121, 124, 125; 128/849, 128/851–852
See application file for complete search history.

(56) References Cited

U.S. PATENT DOCUMENTS

| | | | | |
|---|---|---|---|---|
| 5,080,108 | A | 1/1992 | Roth | |
| 5,122,904 | A | 6/1992 | Fujiwara et al. | |
| 5,970,980 | A | 10/1999 | Adair | |
| 6,091,058 | A | 7/2000 | Faries, Jr. et al. | |
| 6,132,368 | A | 10/2000 | Cooper | |
| 6,375,006 | B1 | 4/2002 | Samuels | |
| 6,586,354 | B1 | 7/2003 | Topolkaraev et al. | |
| 6,671,581 | B2 | 12/2003 | Niemeyer et al. | |
| 6,824,511 | B1 | 11/2004 | Bell et al. | |
| 7,666,191 | B2 | 2/2010 | Orban, III et al. | |
| 7,727,244 | B2 * | 6/2010 | Orban, III .............. | A61B 46/10 600/102 |
| 7,886,743 | B2 | 2/2011 | Cooper et al. | |
| 8,202,278 | B2 | 6/2012 | Orban, III et al. | |
| 8,220,468 | B2 | 7/2012 | Cooper et al. | |
| 8,273,076 | B2 | 9/2012 | Devengenzo et al. | |
| 8,545,515 | B2 | 10/2013 | Prisco et al. | |
| 8,592,582 | B2 | 11/2013 | Fukunishi et al. | |
| 9,060,678 | B2 | 6/2015 | Larkin et al. | |
| 10,932,877 | B2 | 3/2021 | Devengenzo et al. | |
| 11,039,820 | B2 | 6/2021 | Beira | |
| 11,883,123 | B2 * | 1/2024 | Ramstad ................ | A61B 34/30 |
| 12,016,647 | B2 | 6/2024 | Devengenzo et al. | |
| 2006/0235436 | A1 | 10/2006 | Anderson et al. | |
| 2007/0129634 | A1 | 6/2007 | Hickey et al. | |
| 2007/0239172 | A1 | 10/2007 | Lee et al. | |
| 2008/0001559 | A1 | 1/2008 | Schena | |
| 2008/0003555 | A1 | 1/2008 | Ekvall et al. | |
| 2010/0222725 | A1 | 9/2010 | Munzel et al. | |
| 2010/0292707 | A1 | 11/2010 | Ortmaier et al. | |
| 2010/0307942 | A1 | 12/2010 | Tomes et al. | |
| 2011/0217923 | A1 | 9/2011 | Ma | |
| 2011/0277775 | A1 | 11/2011 | Holop et al. | |
| 2011/0277776 | A1 | 11/2011 | McGrogan et al. | |
| 2012/0083768 | A1 | 4/2012 | Skora et al. | |
| 2012/0232566 | A1 | 9/2012 | Orban, III et al. | |
| 2012/0247489 | A1 | 10/2012 | Orban, III et al. | |
| 2013/0199544 | A1 | 8/2013 | Fortier et al. | |
| 2013/0289586 | A1 * | 10/2013 | Mazzucco ............ | A61B 17/083 606/151 |
| 2013/0325031 | A1 | 12/2013 | Schena et al. | |
| 2013/0325033 | A1 | 12/2013 | Schena et al. | |
| 2014/0338676 | A1 | 11/2014 | Marinchak | |
| 2015/0000676 | A1 * | 1/2015 | Colona .................. | A61B 46/00 128/849 |
| 2015/0202009 | A1 | 7/2015 | Nussbaumer et al. | |
| 2016/0184037 | A1 | 6/2016 | Cooper et al. | |
| 2019/0298469 | A1 | 10/2019 | Ramstad et al. | |
| 2021/0267703 | A1 | 9/2021 | Devengenzo et al. | |

FOREIGN PATENT DOCUMENTS

| | | | | | |
|---|---|---|---|---|---|
| CA | 2681965 | A1 | | 3/2003 | |
| CN | 1228688 | A | | 9/1999 | |
| CN | 101095638 | A | | 1/2008 | |
| CN | 101304702 | A | | 11/2008 | |
| CN | 101641044 | A | | 2/2010 | |
| CN | 201414848 | Y | | 3/2010 | |
| CN | 101801301 | A | | 8/2010 | |
| CN | 201823147 | U | | 5/2011 | |
| CN | 102208835 | A | | 10/2011 | |
| CN | 102946819 | A | | 2/2013 | |
| DE | 10122311 | A1 | | 12/2001 | |
| EP | 2559396 | A2 | | 2/2013 | |
| JP | H0586301 | U | | 11/1993 | |
| JP | 2000312685 | A | | 11/2000 | |
| JP | 2001187066 | A | | 7/2001 | |
| JP | 2001208978 | A | | 8/2001 | |
| JP | 2003033371 | A | | 2/2003 | |
| JP | 2003220077 | A | | 8/2003 | |
| JP | 2005237839 | A | | 9/2005 | |
| JP | 2006506128 | A | | 2/2006 | |
| KR | 20110036452 | A | * | 4/2011 | |
| WO | WO-9510986 | A1 | | 4/1995 | |
| WO | WO-2005015703 | A1 | * | 2/2005 | ............... H02G 3/32 |
| WO | WO-2007041093 | A1 | | 4/2007 | |
| WO | WO-2007142698 | A2 | | 12/2007 | |
| WO | WO-2009123925 | A1 | | 10/2009 | |
| WO | WO-2011060046 | A2 | | 5/2011 | |
| WO | WO-2011156875 | A1 | | 12/2011 | |
| WO | WO-2015127231 | A1 | | 8/2015 | |
| WO | WO-2018013236 | A1 | | 1/2018 | |

OTHER PUBLICATIONS

Definition of "Cable" from https://www.thefreedictionary.com/support (Year: 2019).

Definition of "Support" from https://www.thefreedictionary.com/support (Year: 2019).

Extended European Search Report for Application No. EP15765258.7, mailed on Oct. 30, 2017, 9 pages.

Extended European Search Report for Application No. EP22160050.5, mailed on Jul. 29, 2022, 05 pages.

International Search Report and Written Opinion for Application No. PCT/US15/20929, mailed on May 28, 2015, 18 pages.

International Search Report and Written Opinion for Application No. PCT/US2017/038350, mailed on Oct. 12, 2017, 14 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

MECHANISM FOR MANAGING AND RETAINING A SURGICAL DRAPE

CROSS-REFERENCE TO RELATED APPLICATION

This application is a continuation of U.S. patent application Ser. No. 16/317,285 (now U.S. Pat. No. 11,883,123 B2, which is a National Stage Application under 35 U.S.C. § 371 and claims the benefit of International Application No. PCT/US2017/038350, filed Jun. 20, 2017, which claims benefit of U.S. Provisional Application No. 62/362,194, filed Jul. 14, 2016, each of which is hereby incorporated by reference in their entirety.

BACKGROUND

Field of Invention

The present invention relates generally to surgical drapes for computer-assisted surgical systems, and more particularly to mechanisms used in management of a surgical drape during operation of the computer-assisted surgical system.

Description of Related Art

A surgical drape has been previously used to cover a surgical manipulator such as a plurality of surgical instrument manipulator assemblies 140 in computer-assisted surgical system 100. The drapes have taken various forms. In each instance, the manipulator and associated supports links are covered with a surgical drape prior to the start of the surgical procedure.

Surgical system 100 is a computer-assisted surgical system that includes an endoscopic imaging system 192, a surgeon's console 194 (master), and a patient side support system 110 (slave), all interconnected by wired (electrical or optical) or wireless connections 196. One or more electronic data processors may be variously located in these main components to provide system functionality. Examples are disclosed in U.S. Pat. No. 9,060,678 B2 (filed Jun. 13, 2007), which is incorporated by reference herein.

Imaging system 192 performs image processing functions on, e.g., captured endoscopic imaging data of the surgical site and/or preoperative or real time image data from other imaging systems external to the patient. Imaging system 192 outputs processed image data (e.g., images of the surgical site, as well as relevant control and patient information) to a surgeon at surgeon's console 194. In some aspects, the processed image data is output to an optional external monitor visible to other operating room personnel or to one or more locations remote from the operating room (e.g., a surgeon at another location may monitor the video; live feed video may be used for training; etc.).

Surgeon's console 194 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Console 194 also includes a stereoscopic video output display positioned such that images on the display are generally focused at a distance that corresponds to the surgeon's hands working behind/below the display screen. These aspects are discussed more fully in U.S. Pat. No. 6,671,581 B2 (filed Jun. 5, 2002), which is incorporated by reference herein.

Control during insertion of the instruments may be accomplished, for example, by the surgeon moving the instruments presented in the image with one or both of the masters; the surgeon uses the masters to move the instrument in the image side to side and to pull the instrument towards the surgeon. The motion of the masters commands the imaging system and an associated surgical device assembly to steer towards a fixed center point on the output display and to advance inside the patient.

In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control.

Base 101 of patient side support system 110 supports an arm assembly that includes a passive, uncontrolled setup arm assembly 120 and an actively controlled manipulator arm assembly 130. Actively controlled manipulator arm assembly 130 is referred to as entry guide manipulator 130.

In one example, setup assembly 120 includes two passive rotational setup joints 103 and 105. Rotational setup joints 103 and 105 allow manual positioning of coupled setup links 104 and 106 if the joint brakes for setup joints 103 and 105 are released. Alternatively, some of these setup joints may be actively controlled, and more or fewer setup joints may be used in various configurations. Setup joints 103 and 105 and setup links 104 and 106 allow a person to place entry guide manipulator 130 at various positions and orientations in Cartesian x,y,z space. A prismatic setup joint (not shown) between link 104 of arm assembly 120 and base 101 may be used for vertical adjustments 112.

A remote center of motion 146 is a location at which yaw, pitch, and roll axes intersect (i.e., the location at which the kinematic chain remains effectively stationary while joints move through their range of motion). Some of these actively controlled joints are manipulators that are associated with controlling DOFs of individual instruments, and others of these actively controlled joints are associated with controlling DOFs of a single assembly of these manipulators. The active joints and links are movable by motors or other actuators and receive movement control signals that are associated with master arm movements at surgeon's console 194.

As shown in FIG. 1, a manipulator assembly yaw joint 111 is coupled between an end of setup link 106 and a first end, e.g., a proximal end, of a first manipulator link 113. Yaw joint 111 allows first manipulator link 113 to move with reference to link 106 in a motion that may be arbitrarily defined as "yaw" around a manipulator assembly yaw axis 123. As shown, the rotational axis of yaw joint 111 is aligned with remote center of motion 146, which is generally the position at which an instrument enters the patient (e.g., at the umbilicus for abdominal surgery).

In one embodiment, setup link 106 is rotatable in a horizontal or x,y plane, and yaw joint 111 is configured to allow first manipulator link 113 in entry guide manipulator 130 to rotate about yaw axis 123. Setup link 106, yaw joint 111, and first manipulator link 113 provide a constantly vertical yaw axis 123 for entry guide manipulator 130, as illustrated by the vertical line through yaw joint 111 to remote center of motion 146.

A distal end of first manipulator link 113 is coupled to a proximal end of a second manipulator link 115 by a first actively controlled rotational joint 114. A distal end of second manipulator link 115 is coupled to a proximal end of a third manipulator link 117 by a second actively controlled rotational joint 116. A distal end of third manipulator link 117 is coupled to a distal portion of a fourth manipulator link 119 by a third actively controlled rotational joint 118.

In one embodiment, links 115, 117, and 119 are coupled together to act as a coupled motion mechanism. Coupled motion mechanisms are well known (e.g., such mechanisms are known as parallel motion linkages when input and output link motions are kept parallel to each other). For example, if rotational joint 114 is actively rotated, joints 116 and 118 are also actively rotated so that link 119 moves with a constant relationship to link 115. Therefore, it can be seen that the rotational axes of joints 114, 116, and 118 are parallel. When these axes are perpendicular to rotational axis 123 of joint 111, links 115, 117, and 119 move with reference to link 113 in a motion that may be arbitrarily defined as "pitch" around a manipulator assembly pitch axis.

The manipulator pitch axis extends into and out of the page in FIG. 1 at remote center of motion 146, in this aspect. The motion around the manipulator assembly pitch axis is represented by arrow 121. Since links 115, 117, and 119 move as a single assembly, first manipulator link 113 may be considered an active proximal manipulator link, and second through fourth manipulator links 115, 117, and 119 may be considered collectively an active distal manipulator link.

An entry guide manipulator assembly platform 132, sometimes referred to as platform 132, is coupled to a distal end of fourth manipulator link 119. An entry guide manipulator assembly 133 is rotatably mounted on platform 132. Entry guide manipulator assembly 133 includes an instrument manipulator positioning system.

Entry guide manipulator assembly 133 rotates plurality of surgical instrument manipulator assemblies 140 as a group around axis 125. Specifically, entry guide manipulator assembly 133 rotates as a single unit with reference to platform 132 in a motion that may be arbitrarily defined as "roll" around an entry guide manipulator assembly roll axis 125.

Each of a plurality of surgical instrument manipulator assemblies 140 is coupled to entry guide manipulator assembly 133 by a different insertion assembly 135. In one aspect, each insertion assembly 135 is a telescoping assembly that moves the corresponding surgical instrument manipulator assembly away from and towards entry guide manipulator assembly 133. In FIG. 1, each of the insertion assemblies is in a fully retracted position.

Each of the plurality of surgical instrument manipulator assemblies includes a plurality of motors that drive a plurality of outputs in an output interface of that surgical instrument manipulator assembly. See U.S. Patent Application Publication No. US 2016/0184037 A1 (filed Aug. 13, 2014), which is incorporated by reference, for one example of a surgical instrument manipulator assembly and a surgical instrument that can be coupled to the surgical instrument manipulator assembly.

In one aspect, a membrane interface that is part of a surgical drape may be placed between the instrument mount interface of a surgical instrument manipulator assembly and the input interface of the transmission unit of a corresponding surgical instrument. See U.S. Patent Application Publication No. US 2011/0277776 A1 (filed Aug. 12, 2010) for an example of the membrane interface and surgical drape. In another aspect, a sterile adapter that is part of a surgical drape may be placed between the instrument mount interface of the surgical instrument manipulator assembly and the input interface of the transmission unit of the corresponding surgical instrument. See U.S. Patent Application Publication No. US 2011/0277775 A1 (filed Aug. 12, 2010) for an example of a sterile adapter and a surgical drape.

FIG. 2 is a perspective view of a drape portion 200 of an extended surgical drape including a sterile adapter 250. Drape portion 200 includes a plurality of drape sleeves 205 coupled between rotatable seal 208 and sterile adapter 250.

Rotatable seal 208 operably couples proximal openings 203 of plurality of drape sleeves 205 to the manipulator platform of the manipulator arm assembly. In one example, rotatable seal 208 includes a rotatable labyrinth seal having a roll cover portion **208*a* and a base comb portion 208*b*. Base comb portion 208*b* is rotatable relative to roll cover portion 208*a*. Base comb portion 208*b* includes a disc with ribs 204 that form a plurality of wedge-shaped "frames" with apertures. Each of the frames is sized to circumscribe a surgical instrument manipulator assembly. A proximal end of each of plurality of drape sleeves 205 is coupled to a different one of the plurality of wedge-shaped frames of base comb portion 208*b*. Ribbed base comb portion 208*b* aids in draping each individual one of the surgical instrument manipulator assemblies, which are closely clustered on the rotatable base plate of entry guide manipulator assembly 133, and further aids in maintaining the orientation and arrangement of each of the plurality of drape sleeves 205** as the draped surgical instrument manipulator assemblies move during a surgical procedure.

Although FIG. 2 illustrates each of plurality of drape sleeves 205 in an extended state, for example as the surgical instrument manipulator assemblies extend along their respective insertion mechanisms, each of plurality of drape sleeves 205 may independently retract and extend as a corresponding surgical instrument manipulator assembly is independently and/or dependently controlled with respect to the other surgical instrument manipulator assemblies.

Roll cover portion **208*a* fixedly mounts to frame of manipulator platform 132 (e.g., the manipulator halo), and base comb portion 208*b* fixedly mounts to the rotatable base plate of entry guide manipulator assembly 133, such that when the rotatable base plate of entry guide manipulator assembly 133 is rotated, base comb portion 208*b* also rotates in combination with the draped surgical instrument manipulator assemblies. Since the proximal end of each of plurality of drape sleeves 205 is coupled to base comb portion 208*b*, all the drape sleeves 205 rotate together as a group with reference to a more proximal drape portion 210**.

SUMMARY

A cinch assembly is affixed to a surgical drape to manage excess surgical drape material so that the sterility of sterile portions of the surgical drape is not compromised, and so that the integrity of surgical drape is not compromised. The cinch assembly includes a pair of links joined by a hinge joint. In one aspect, an alignment and attachment element is also affixed to the surgical drape.

In another aspect, the cinch assembly is included in a hinged cinch and attachment element assembly. The hinged cinch and attachment element assembly also includes an attachment element mounted on one link of the pair of links. The hinge joint is a living hinge, in one aspect. The hinged cinch and attachment element assembly includes a first connector component mounted over a first link of the pair of links, and a second connector component mounted over a second link of the pair of links. The first connector component is configured to mate with the second connector component.

In yet another aspect, the cinch assembly includes a first folding mechanism, a second folding mechanism, and an elongate member coupling the first folding mechanism to the second folding mechanism. The second folding mechanism includes a plurality of links, with each pair of links of the plurality of links being connected by a hinge joint. The cinch assembly also includes a first connector component mounted over a first link of the plurality of links. The first link is adjacent the elongate member. A second connector component is mounted over a second link of the plurality of links. The second link is a link of the plurality of links most removed from the elongate member.

In a still further aspect, a structure includes a surgical drape, a first assembly affixed to the surgical drape, a second assembly affixed to the surgical drape, and a third assembly affixed to the surgical drape. In one aspect, the first assembly is a cinch assembly, the second assembly is a hinged cinch and attachment element assembly, and the third assembly is an alignment and attachment element assembly.

The hinged cinch and attachment element assembly includes a pair of links joined by a hinge joint and an attachment element mounted on one of the pair of links. A first connector component is mounted over a first link of the pair of links. A second connector component is mounted over a second link of the pair of links. The first connector component is configured to mate with the second connector component.

The cinch assembly includes a first folding mechanism, a second folding mechanism, and an elongate member coupling the first folding mechanism to the second folding mechanism. The first folding mechanism includes a first plurality of links, with each pair of the first plurality of links being connected by a hinge joint. Similarly, the second folding mechanism includes a second plurality of links, with each pair of the second plurality of links being connected by a hinge joint. A first connector component is mounted over a first link of the second plurality of links, where the first link is adjacent the elongate member. A second connector component is mounted over a second link of the second plurality of links. The second link is a link of the second plurality of links most removed from the elongate member. The first connector component is configured to mate with the second connector component.

A surgical support system includes a first link and a second link. The first link includes an end including a drape guide lip. The second link is coupled to the first link, and the second link is configured to move under the drape guide lip.

Figure 1:
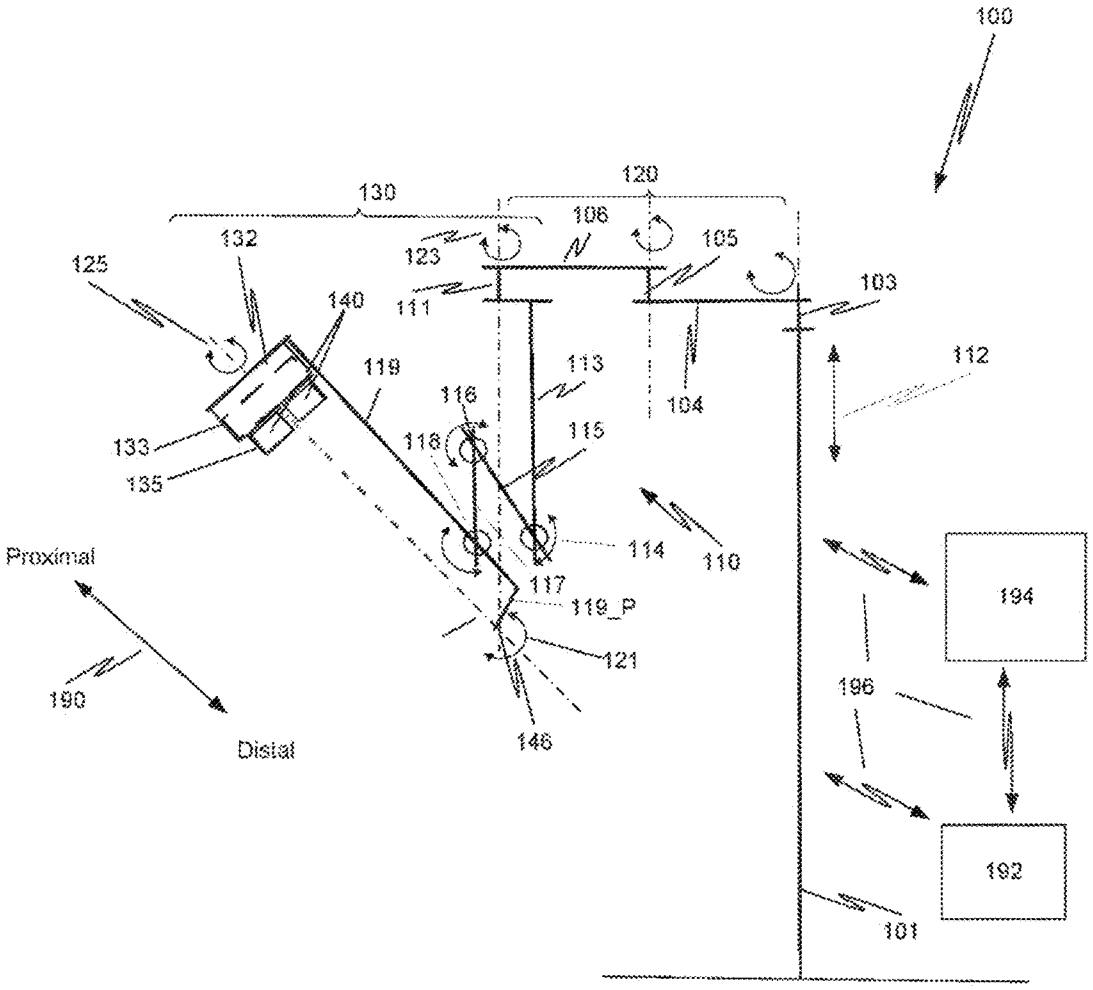
Fig. 1 (Prior Art)
FIG. 1 is an illustration of a prior art computer-assisted surgical system.
Figure 2:
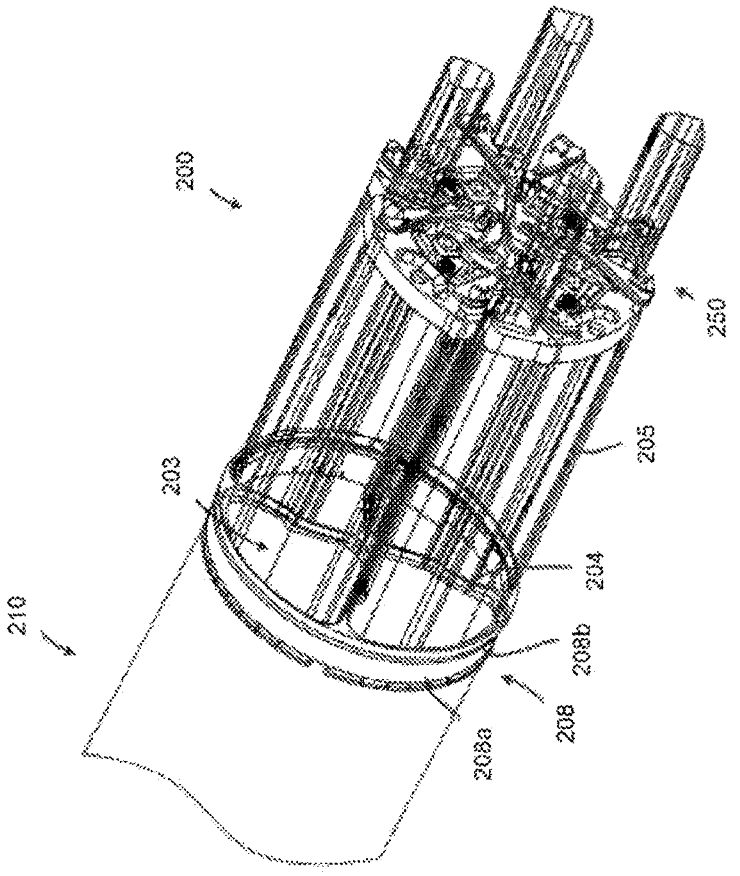
Fig. 2 (Prior Art)
FIG. 2 is a representation of one example of a prior art surgical drape.

In the drawings, the first digit in a three-digit reference numeral of an element is the number of the figure in which that element first appears, and the first two digits in a four-digit reference numeral of an element is the number of the figure in which that element first appears.

DETAILED DESCRIPTION

In one aspect, a sterile surgical drape 360 (FIG. 3), sometimes referred to as surgical drape 360, is enhanced by including at least one assembly for managing and retaining sterile surgical drape 360 on a part of a computer-assisted surgical system. For example, a plurality of assemblies 366 (also mechanisms 366) for managing and retaining sterile surgical drape is used to configure surgical drape 360 on a portion of the computer-assisted surgical system, e.g., patient side support system 410 (FIG. 4), so that the sterility of sterile portions of surgical drape 360 is not compromised.

Sterile surgical drape 360 includes a sterile outer side (a first side) and an inner side (a second side), which is not treated as sterile. When surgical drape 360 is mounted on a part of a computer-assisted surgical system, the second side is against the part of the computer-assisted surgical system.

Typically, surgical drape 360 must be large enough to go around and cover the largest portion of computer-assisted surgical system that is draped. This means that there is excess drape material when surgical drape 360 is fully deployed over at least some of the components of a surgical support system.

It is important that the sterile outside of the drape not contact any part of the computer-assisted surgical system during draping or operation of the computer-assisted surgical system, because this contact would contaminate the sterile side. Also, it is important that any excess drape material not be snagged or otherwise engaged with any portion of the computer-assisted surgical system during a surgical procedure because this could compromise the physical integrity (i.e., rip, tear, puncture) of surgical drape 360. A plurality of assemblies 366 for managing and retaining sterile surgical drape material solves these problems.

In one aspect, a cinch assembly is affixed to surgical drape 360. Typically, the cinch assembly includes a pair of links joined by a hinge joint. The cinch assembly is configured to fold and hold excess drape material so that surgical drape 360 is cinched to the structure draped by surgical drape 360.

As explained more completely below, in one aspect, the cinch assembly is a hinged cinch and attachment element assembly 368 that is affixed to surgical drape 360. Hinged cinch and attachment element assembly 368 includes a hinged cinch and an attachment element. The hinged cinch includes a pair of links joined by a hinge joint. The attachment element is mounted on one link of the pair of links. In one aspect, the hinge joint is a living hinge.

Hinged cinch and attachment element assembly 368 also includes a first connector component mounted on the surgical drape opposite a first link of the pair of links, e.g., the first connector component is mounted over the first link, and a second connector component mounted on the surgical drape opposite a second link of the pair of links, e.g., the second connector component is mounted over the second link. The first connector component is configured to mate with the second connector component.

In another aspect, a cinch assembly 367 is affixed to surgical drape 360. Cinch assembly 367 includes a first folding mechanism, a second folding mechanism, and an elongate member connecting the first folding mechanism to the second folding mechanism. The first folding mechanism includes a first plurality of links, where each pair of links of the first plurality of links is connected by a hinge joint. Similarly, the second folding mechanism includes a second plurality of links, where each pair of links of the second plurality of links is connected by a hinge joint. Cinch assembly 367 includes a first connector component mounted over a first link of the second plurality of links, the first link being adjacent the elongate member, and a second connector component mounted over a second link of the second plurality of links, the second link being a link of the second plurality of links most removed from the elongate member. Cinch assembly 367 also includes a third connector component mounted over a first link of the first plurality of links, the first link of the first plurality of links being adjacent the elongate member, and a fourth connector component mounted over a second link of the first plurality of links, the second link being a link of the first plurality of links most removed from the elongate member.

Here, the first link being adjacent the elongate member means the first link of the folding mechanism is directly connected to the elongate member. The second link being the link most removed from the elongate member means that the second link is the link of the folding mechanism that is farthest from the elongate member along a lengthwise axis of the cinch assembly.

Figure 3:
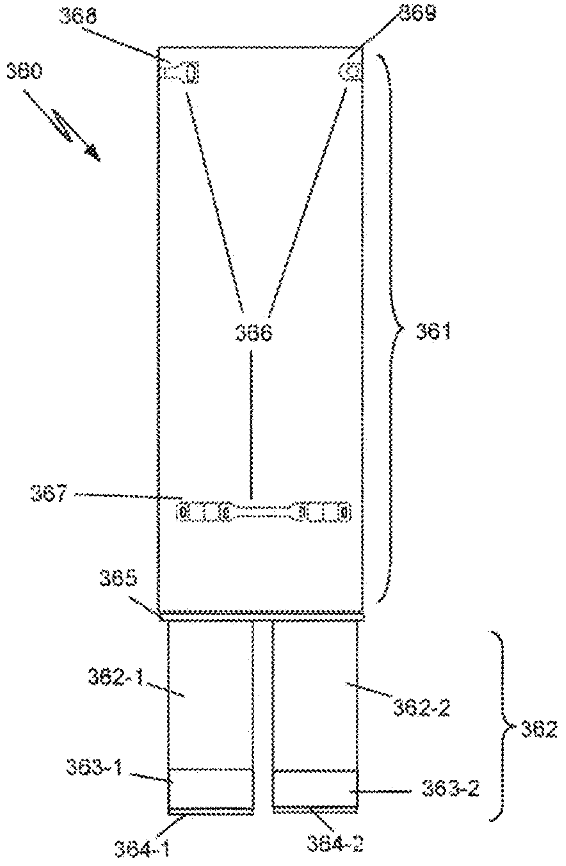
FIG. 3 is an example of a surgical drape that includes a plurality of assemblies for managing and retaining a sterile surgical drape on part of a computer-assisted surgical system.

Thus, in the aspect illustrated in FIG. 3, plurality of assemblies 366 for managing and retaining sterile surgical drape includes a first assembly, a second assembly, and a third assembly. The first assembly is hinged cinch assembly 367, the second assembly is hinged cinch and attachment element assembly 368 (only partially visible; see FIG. 9), and the third assembly is an alignment and attachment element assembly 369 (only partially visible; see FIG. 11).

The use of a plurality of assemblies 366 for managing and retaining sterile surgical drape 360 is optional. Other surgical drapes may use any one of hinged cinch assembly 367, hinged cinch and attachment element assembly 368, and alignment and attachment element assembly 369, or any combination of hinged cinch assembly 367, hinged cinch and attachment element assembly 368, and alignment and attachment element assembly 369.

As explained more completely below, in this aspect hinged cinch assembly 367 is attached to the inside of surgical drape 360. In another aspect, hinged cinch assembly 367 is attached to the outside of surgical drape 360. Hinges of hinged cinch assembly 367 are manipulated to fold excess drape material and to hold the folded excess drape material in place, so that surgical drape 360 is cinched around entry guide manipulator assembly platform 432 (FIG. 4), sometimes referred to as platform 432.

Figure 4:
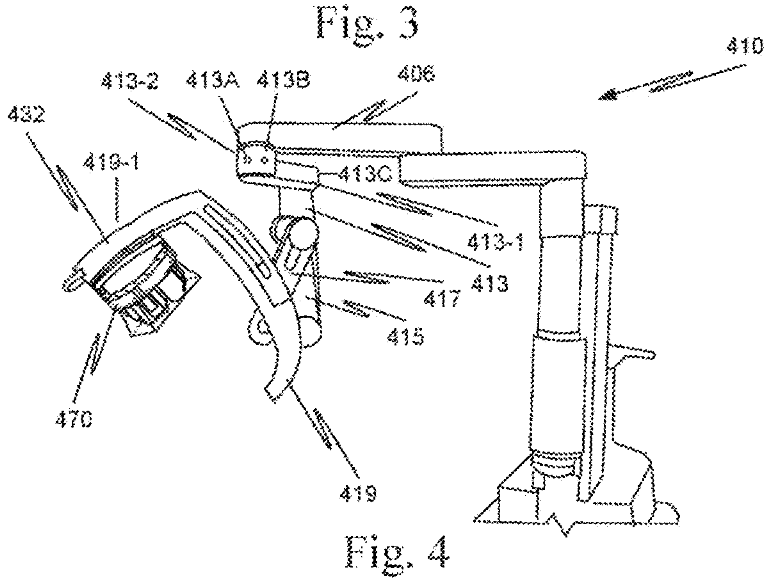
FIG. 4 is an illustration of a computer-assisted surgical system that includes the surgical drape of FIG. 3 mounted on the system prior to draping of the system.
Figure 8A:
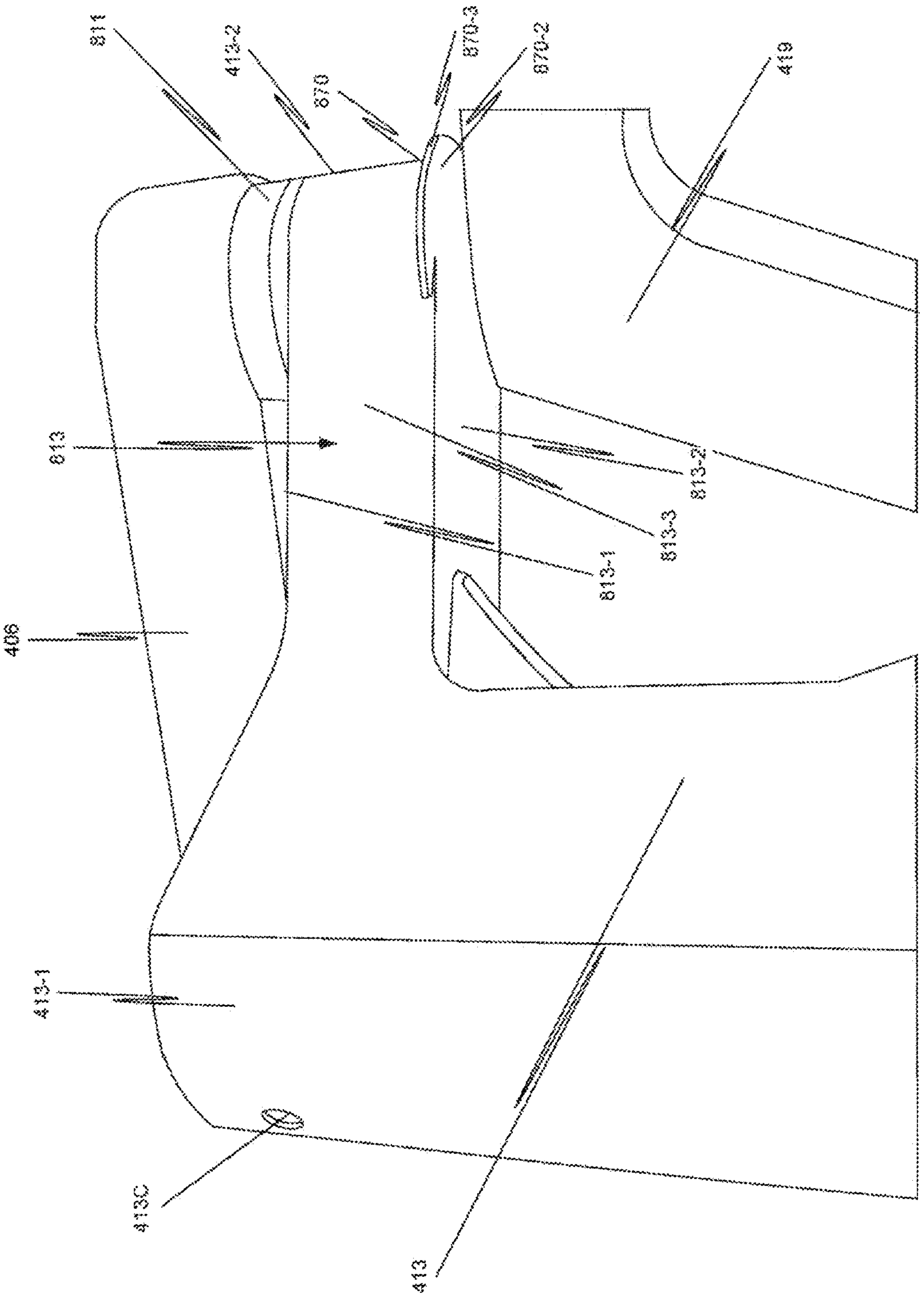
FIGS. 8A and 8B illustrate a drape guide lip on an end of a first active link of the computer-assisted surgical system of FIG. 4 as well as the limited clearance between the first active link and another link of the computer-assisted surgical system.
Figure 8B:
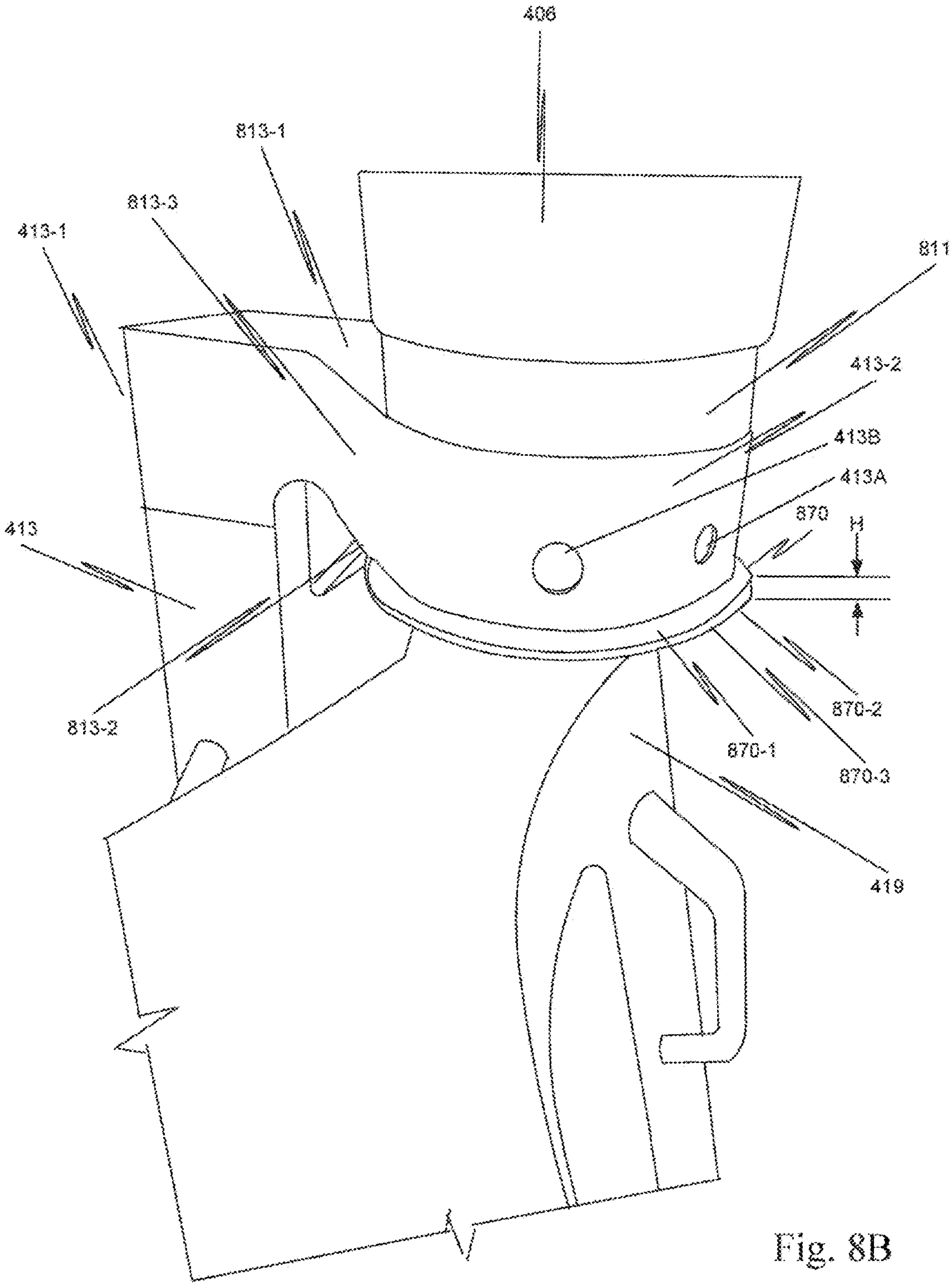

In one aspect, a first active manipulator link 413, sometimes referred to as link 413, includes a first end 413-1 that includes an alignment receptacle 413C (see FIG. 8A) and a second end 413-2 that includes two alignment receptacles 413A,413B (FIGS. 4 and 8B). Alignment and attachment element assembly 369 is affixed to surgical drape 360. Alignment and attachment element assembly 369 includes a first attachment element that fits in alignment receptacle 413A and a second attachment element that fits in alignment receptacle 413B. When one of the first attachment element and the second attachment element of alignment and attachment element assembly 369 is placed in the corresponding receptacle in first active manipulator link 413, the other of the first attachment element and second attachment element of alignment and attachment element assembly 369 is automatically aligned with and placed in in the corresponding receptacle in first active manipulator link 413. The use of two attachment elements separated by a distance makes it easier to secure the open end of sterile surgical drape 360 in the proper orientation and reduces the risk that the attachment will fail and the drape will be contaminated as the remainder of the drape is attached to link 413.

Hinged cinch and attachment element assembly 368, sometimes referred to as assembly 368, is attached to surgical drape 360. As explained more completely below, hinged cinch and attachment element assembly 368, as implied by its name, includes an alignment element and a hinged cinch. The attachment element of assembly 368 pairs with alignment receptacle 413C in first end 413-1 of first link 413. The hinged cinch folds excess drape material and holds the excess drape material folded so that drape 360 is cinched around the horizontal leg of link 413.

In one aspect, sterile surgical drape 360 includes a first portion 361 and a second portion 362. Plurality of assemblies 366 for managing and retaining sterile surgical drape, including a first assembly 367, a second assembly 368, and a third assembly 369, is affixed to first portion 361.

First portion 361 of sterile surgical drape 360 is connected to a stationary part of a rotatable seal 365, and second portion 362 is connected to a movable part of rotatable seal 365. In one aspect, rotatable seal 365 is labyrinth seal, where the stationary part is a roll cover portion of the labyrinth seal, and the movable part is a base comb portion of the labyrinth seal.

Second portion 362 of sterile surgical drape 360, in one aspect, includes a plurality of drape sleeves 362-1, 362-2, a plurality of boots 363-1, 363-2, and a plurality of mechanical interface elements 364-1 364-2. In one aspect, the plurality of mechanical interface elements are each a flexible membrane, such as that described in U.S. Patent Application Publication No. US 2011/0277776 A1. In another aspect, the plurality of mechanical interface elements are each a sterile adapter, such as that described in U.S. Patent Application Publication No. US 2011/0277775 A1.

Each of the plurality of mechanical interface elements 364-1,364-2 is coupled to a corresponding boot in plurality of boots 363-1,363-2. Each of plurality of boots 363-1,363-2 is coupled to a corresponding drape sleeve in plurality of drape sleeves 362-1,362-2. An opening of each drape sleeve in plurality of drape sleeves 362-1,362-2 is connected to the movable portion of rotatable seal 365, which in one aspect is a disc with ribs that form a plurality of wedge-shaped "frames" with apertures. Each of the frames is sized to circumscribe a surgical instrument manipulator assembly. The open end of each of plurality of drape sleeves 362-1, 362-2 is coupled to a different one of the plurality of wedge-shaped frames. Each of plurality of boots 363-1, 363-2 fits around a surgical instrument manipulator assembly that is coupled by an insertion mechanism to an entry guide manipulator assembly rotatably mounted on platform 432.

Except as described more completely below, the configuration and operation of links 406, 413, 415, 417, 419, platform 432, the entry guide manipulator assembly, the insertion mechanisms, and the plurality of surgical instrument manipulator assemblies of patient side support system 410 are the same as the configuration and operation of links 106, 113, 115, 117, 119, platform 132, entry guide manipulator assembly 133, insertion mechanisms 135, and plurality of surgical instrument manipulator assemblies 140 of patient side support system 110. Thus, the description of the configuration and operation of links 106, 113, 115, 117, 119, platform 132, entry guide manipulator assembly 133, insertion mechanisms 135, and plurality of surgical instrument manipulator assemblies 140 of patient side support system 110 is not repeated here for the configuration and operation of links 406, 413, 415, 417, 419, platform 432, the entry guide manipulator assembly, the insertion mechanisms, and the plurality of surgical instrument manipulator assemblies of patient side support system 410.

In one aspect, a surgical drape installation package 470 (FIG. 4), which includes surgical drape 360 packaged in a surgical drape installation aid, is mounted on patient side support system 410 so that the stationary part of rotatable seal 365 is mounted on a distal end of entry guide manipulator assembly platform 432, which is at a first end 419-1 of a fourth active manipulator link 419. For example, latch elements of the stationary part of rotatable seal 365 engage latch receptacles in entry guide manipulator assembly platform 432. For an example of a surgical drape installation package, see commonly filed and commonly assigned U.S. Provisional Patent Application No. 62/362,190 (filed Jul. 14, 2016) "Surgical Drape Installation Aid", which is incorporated herein by reference.

To deploy first portion 361 of surgical drape 360, the first portion is moved over each of manipulator links 419, 417, 415, and 413. Then, first portion 361 is attached to second end 413-2 of first manipulator link 413 by using alignment and attachment element assembly 369 and is attached to first end 413-1 of first manipulator link 413 by using hinged cinch and attachment element assembly 368. With drape 360 held in place around the horizontal leg of link 413, the cinch of hinged cinch and attachment element assembly 368 is used to gather up and secure the excess drape material.

Figure 5:
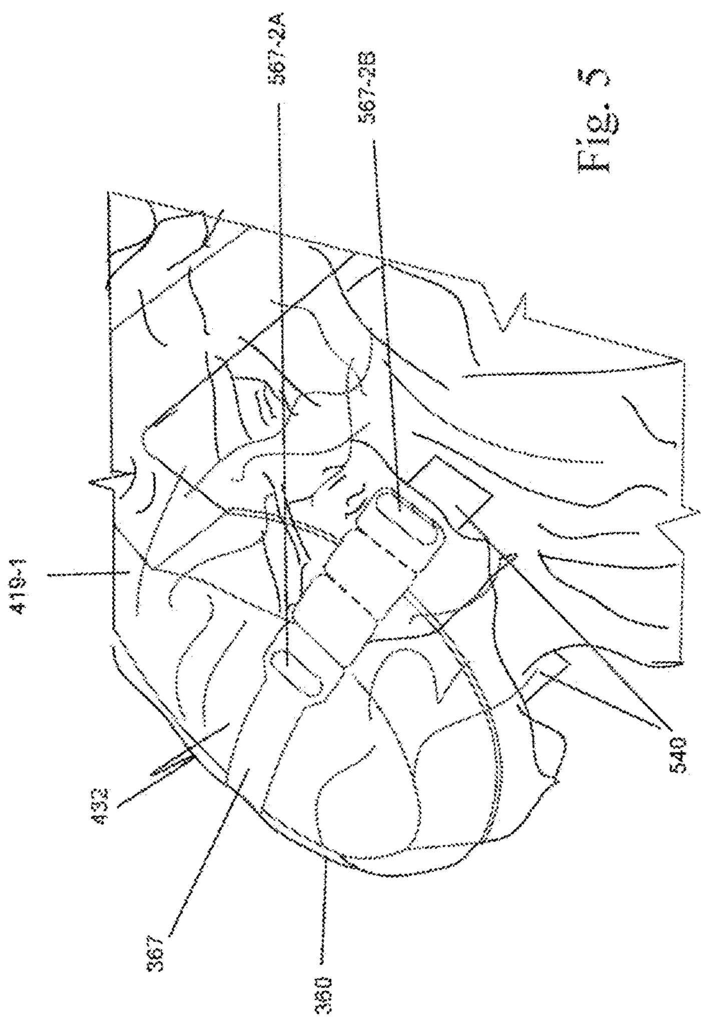
FIG. 5 is an illustration of the surgical drape draped over a part of the computer-assisted system of FIG. 4 before a cinch assembly is used to manage the excess drape material.

FIG. 5 is an illustration showing a portion of drape 360, which deployed over first end 419-1 of a fourth manipulator link 419. A plurality of surgical instrument manipulators 540 is visible in FIG. 5. Plurality of surgical instrument manipulator assemblies 540 is equivalent to plurality of surgical instrument manipulator assemblies 140, and so the description of plurality of surgical instrument manipulator assemblies 140 is not repeated here.

Figure 6:
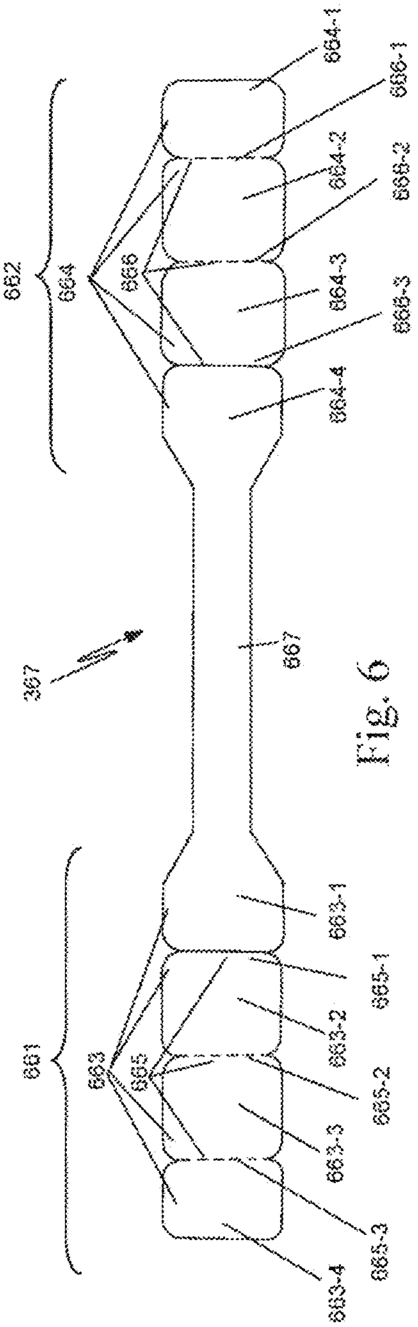
FIG. 6 is an illustration of a part of the cinch assembly.

Only a portion of hinged cinch assembly 367 is visible in FIG. 5. A more detailed illustration of hinged cinch assembly 367 is presented in FIG. 6. Hinged cinch assembly 367 is affixed to the inner side of surgical drape 360 by using double-sided pressure-sensitive tape, in this aspect. To position hinged cinch assembly 367 on the proper location of the inner surface of surgical drape, a template is used.

In one aspect, hinged cinch assembly 367 is made from a high strength, moderate stiffness material, e.g., high density polyethylene (HDPE). But, a heat molded material or any material that has properties which allow the cinching action could be used. Here, moderate stiffness means the material retains its shape during the cinching action, but the material conforms to the shape of an object on which the material rests.

Hinged cinch assembly 367 includes an elongate member 667, e.g., a strip, with a folding mechanism 661,662 on each end of elongate member 667, sometimes referred to as strip 667. Each of folding mechanisms 661,662 includes a plurality of links 663,664 and a plurality of hinge joints 665,666. There is a hinge joint between each different pair of links.

More specifically, folding mechanism 661 includes a first link 663-1 that is affixed to a first end of elongate member 667. First link 663-1 is adjacent elongate member 667. A first hinge joint 665-1 couples first link 663-1 to a second link 663-2. A second hinge joint 665-2 couples second link 663-2 to a third link 663-3. A third hinge joint 665-3 couples third link 663-3 to a fourth link 663-4. Fourth link 663-4 is the link most distant from elongate member 667.

Similarly, folding mechanism 662 includes a first link 664-1 that is affixed to a second end of elongate member 667. A first hinge joint 666-1 couples first link 664-1 to a second link 664-2. A second hinge joint 666-2 couples second link 664-2 to a third link 664-3. A third hinge joint 666-3 couples third link 664-3 to a fourth link 664-4.

In one aspect, each of first plurality of hinge joints 665, and each of second plurality of hinge joints 666, is a living hinge. Each living hinge is formed by scoring the region between two adjacent links on one side of hinged cinch assembly 367. The side of hinged cinch assembly 367 that is scored is determined by the direction in which the hinge is desired to pivot.

As shown in FIG. 5, a connector 567-2 includes a first connector component 567-2A positioned over a first link (a link adjacent elongate member 667) of the plurality of links in a folding mechanism and a second connector component 567-2B positioned over a last link (a link most distant from elongate member 667) of the plurality of links in a folding mechanism. In this aspect, first and second connector components 567A, 567B are attached to the sterile side—the outside—of surgical drape 360 over the corresponding link in the folding mechanism.

In one aspect, connector component 567-2A is a piece of loop fabric that has an adhesive backing, and connector component 567-2B is a piece of hook fabric that has an adhesive backing. An example of hook fabric and loop fabric is a nylon fastening tape consisting of two strips of nylon fabric, one having tiny hooked threads and the other having a coarse looped surface. The two strips form a strong bond when pressed together. On example of a commercially available fastening tape is VELCRO® fastening tape. (VELCRO® is a registered trademark of Velcro Industries B.V.)

Figure 7A:
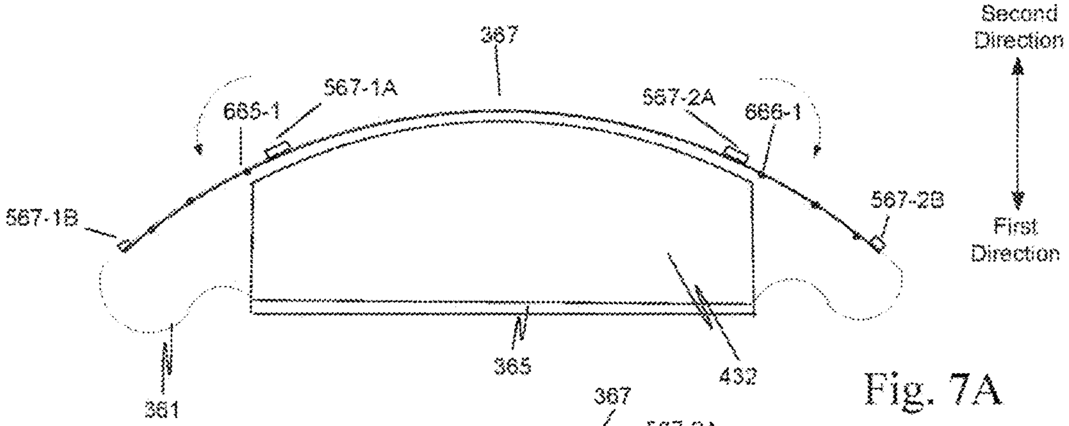
FIGS. 7A to 7D illustrate the use of the cinch assembly to manage the excess drape material.
Figure 7B:
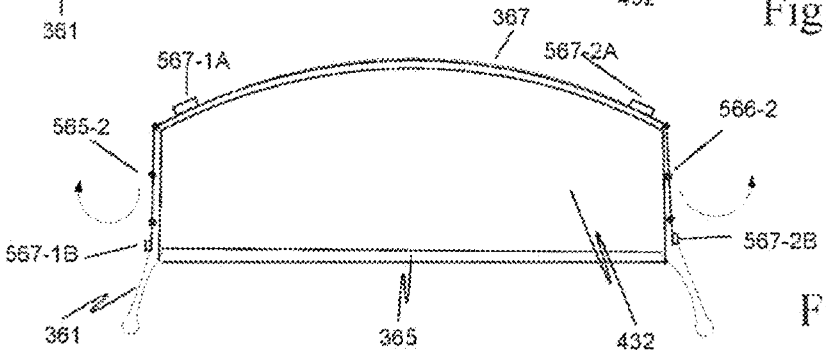
Figure 7C:
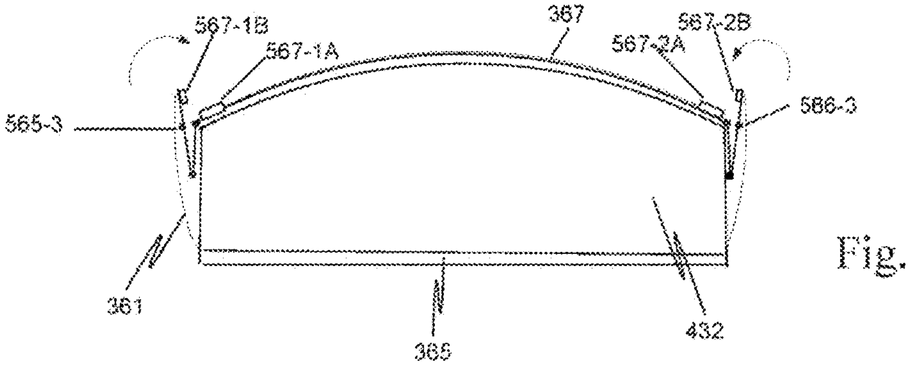
Figure 7D:
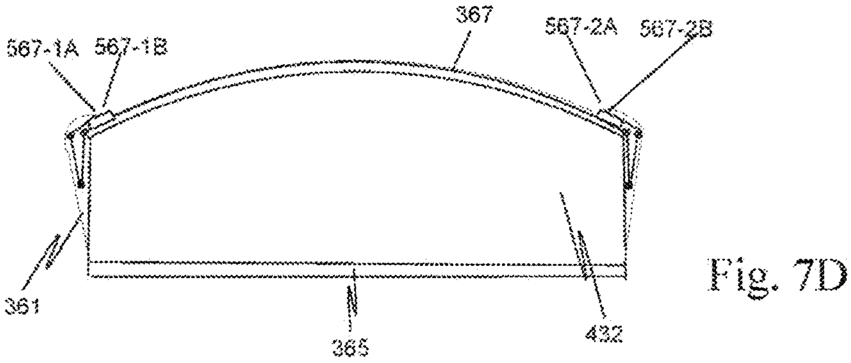

FIGS. 7A to 7D illustrate the operation of hinged cinch assembly 367. In FIGS. 7A to 7B, hinged cinch assembly 367 actually rests on the upper surface of entry guide manipulator assembly platform 432, but for clarity hinged cinch assembly 367 is shown as slightly displaced from the upper surface of entry guide manipulator assembly platform 432.

As explained above, first portion 361 of surgical drape 360 is affixed to a stationary part of a rotatable seal 365. The stationary part of rotatable seal 365 is attached to entry guide manipulator assembly platform 432. As shown in FIG. 7A, there is excess material of first portion 361 of surgical drape 360 that needs to be managed so that the excess material does not hinder the operation of the computer-assisted surgical system by becoming snagged or entangled with a part of patient side support system 410, and so that the sterility of surgical drape 360 is not compromised.

Initially, the second, third, and fourth links of each folding mechanism 661, 662 are pivoted in a first direction around first hinge joint 665-1, 666-1 in that folding mechanism. In this example, the second, third, and fourth links are pivoted until the links are adjacent a sidewall of entry guide manipulator assembly platform 432. This creates a first fold in first portion 361 of surgical drape 360.

Next, the third and fourth links of each folding mechanism 661, 662 are pivoted in a second direction around second hinge joint 665-2, 666-2 in that folding mechanism. The third and fourth links are pivoted until the third link is adjacent to the second link. This creates a second fold in first portion 361 of surgical drape 360.

Finally, the fourth link of each folding mechanism 661, 662 is pivoted in the second direction around third hinge joint 665-3,666-3 in that folding mechanism. The fourth link is pivoted until the connector is connected, e.g., connector component 567-1B engages connector component 567-1A, and connector component 567-2B engages connector component 567-2A. This creates a third fold in first portion 361 of surgical drape 360, and it maintains all the folds in place so that surgical drape portion 361 is cinched to entry guide manipulator assembly platform 432. Thus, the excess drape material about entry guide manipulator assembly platform 432 is cinched to entry guide manipulator assembly platform 432 by using hinged cinch assembly 367.

FIGS. 8A and 8B are illustrations of a part of patient side support system 410. In particular, alignment receptacle 413C in end 413-1 of first link 413 is visible in FIG. 8A. Alignment receptacles 413A and 413B in end 413-2 of first link 413 are visible in FIG. 8B. Also, joint 811 that is connected between link 406 and link 413 is shown. Joint 811 is equivalent to joint 111 (FIG. 1), and so the description of joint 111 is not repeated here for joint 811.

Figure 9:
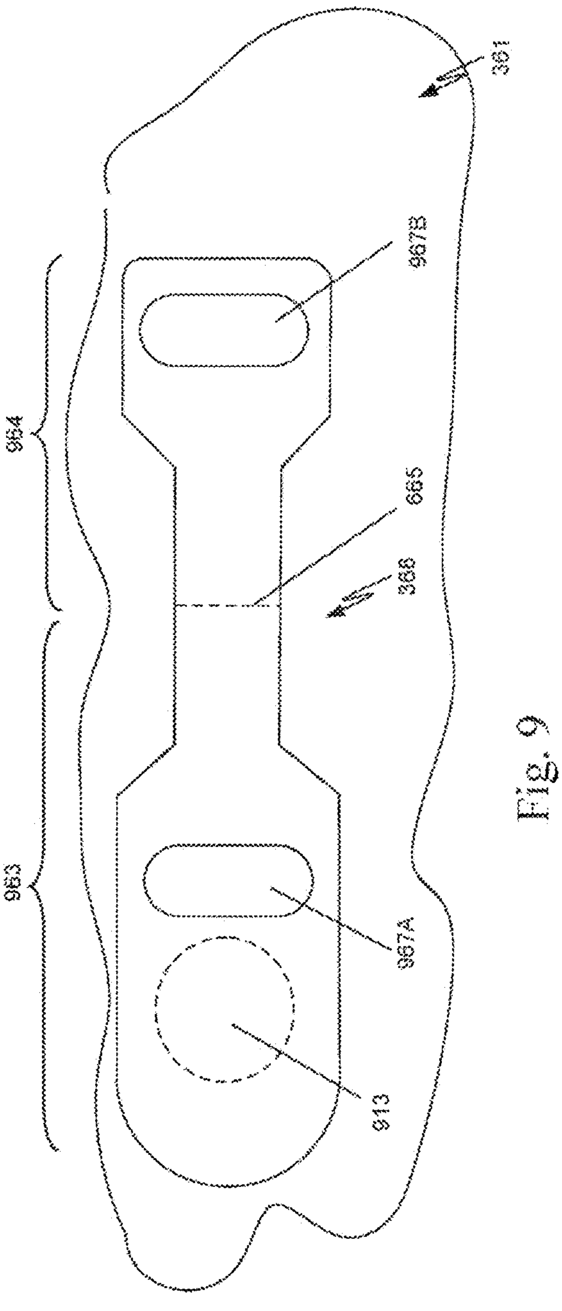
FIG. 9 is an illustration of a hinged cinch and attachment element assembly.

FIG. 9 is an illustration of a part of first portion 361 of surgical drape 360 that includes hinged cinch and attachment element assembly 368. In this aspect, hinged cinch and attachment element assembly 368 is affixed to the inner side of surgical drape 360 with double-sided pressure sensitive tape, but it also could be affixed to the outer side of surgical drape 360 or between layers of surgical drape 360, in a cuff region. To position hinged cinch and attachment element assembly 368 at the proper location on the surface of surgical drape, a template is used.

In one aspect, hinged cinch and attachment element assembly 368 is made from a high strength moderate stiffness material, e.g., high density polyethylene (HDPE). But, a heat molded material or any material that has properties which allow the cinching action could be used.

Hinged cinch and attachment element assembly 368 includes a first link 963 and a second link 964 that are coupled by a hinge joint 665, i.e., the hinge joint is between first link 963 and second link 964. In one aspect, hinge joint 665 is a living hinge. The living hinge is formed by scoring a region between links 963 and 964 in a direction perpendicular to a lengthwise axis of hinged cinch and attachment element assembly 368.

Adjacent an end of link 963 that is removed from hinge joint 665 is an attachment element 913. Attachment element 913 is affixed using double-sided pressure sensitive tape to first link 963 adjacent an end of link 963 most removed from hinge joint 665. In this aspect, attachment element 913 is affixed to the side (a second side) of link 963 that is opposite to the side (a first side) of link 963 attached to the inside surface of surgical drape portion 361. Attachment element 913 fits in attachment receptacle 413C to secure first drape portion 361 to first link 413. In one aspect, attachment receptacle 413C is magnetized, and attachment element 913 is a metal disc that is held in attachment receptacle 413C by the magnetism.

A connector of hinged cinch and attachment element assembly 368 includes a first connector component 967A positioned over first link 963 and a second connector component 967B positioned over second link 964. First and second connector components 967A, 967B are attached to the outside of surgical drape 360 over the corresponding link in the folding mechanism. In one aspect, first connector component 967A is a piece of adhesive-backed loop fabric, and second connector component 967B is a piece of adhesive-backed hook fabric.

Figure 10:
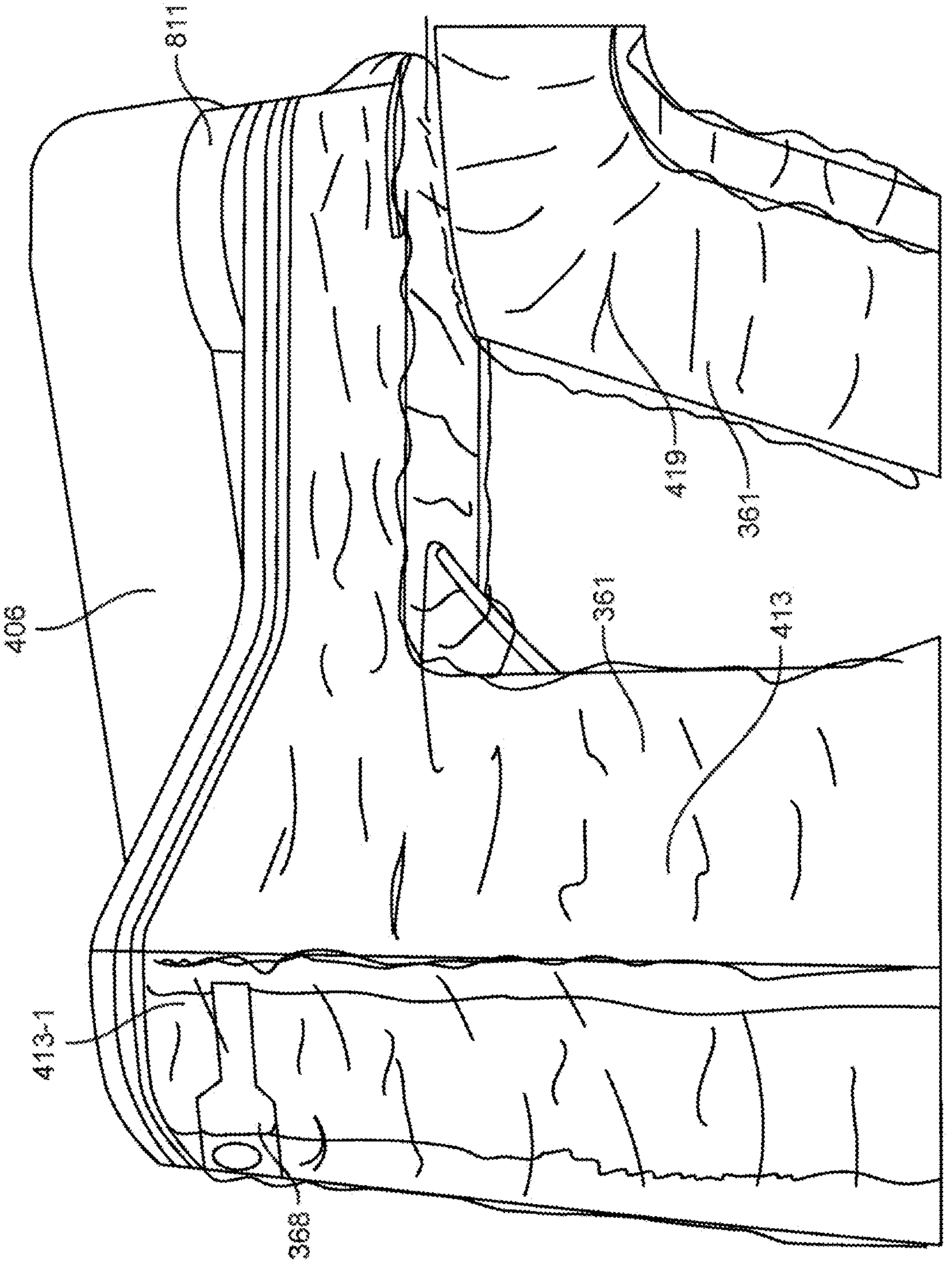
FIG. 10 is an illustration of the first active link after being draped and hinged cinch and attachment element assembly being used to manage excess drape material.

To accordion fold excess material around link 413, link 964 is rotated, e.g., folded back over link 963, until first connector component 967A engages second connector component 967B. When first connector component 967A and second connector component 967B are engaged, the excess drape material is retained in the accordion folds. FIG. 10 shows first drape portion 361 after hinged cinch and attachment element assembly 368 is used to compact the excess drape material in a location that will not interfere with operation of patient side support system 410.

FIG. 4 shows a typical configuration of patient side support system 410 for attaching surgical drape to entry guide manipulator assembly platform 432 and for draping links 413, 415, 417, and 419 by using first portion 361 of surgical drape 360. In some instances, to facilitate draping the surgical instrument manipulator assemblies and insertion mechanisms with second portion 362 of surgical drape 360, fourth link 419 is moved so that the bottom face of entry guide manipulator assembly platform 432 is approximately parallel to the floor. This means that link 419 moves back under the horizontal leg of first link 413.

As shown in FIGS. 8A and 8B, the clearance between links 419 and 413 is limited. To assure that drape 360 does not become entangled on link 413 and does not bunch up and contact a non-sterile component, a drape guide lip 870 extends from curved second end 413-2 of first link 413. Drape guide lip 870 guides any excess drape material on fourth link 419 under link 413 so that drape 360 does not catch on first link 413 and compromise the physical integrity of drape 360 by, for example, tearing drape 360. Drape guide lip 870 also prevents the sterile portion of surgical drape 360 from contacting a non-sterile portion of surgical drape 360 above drape guide lip 870.

Leg 813 of first link 413 has a top surface 813-1 (a first surface) and a bottom surface 813-2 (a second surface) that are connected by a side surface 813-3. Curved end 413-2 is an end of leg 813. In this aspect, leg 813 also is curved.

Bottom surface 813-2 of leg 813 and bottom surface 870-2 (a second surface) of drape guide lip 870 are in a same plane. A side surface 870-3 of drape guide lip 870 extends from bottom surface 870-2 in a direction perpendicular to bottom surface 870-2 for a distance H. In this aspect, side surface 870-3 curves around curved end 413-2 of leg 813. A top surface 870-1 of drape guide lip 870 extends from an intersection with side surface 870-3 to an intersection with side surface 813-3 of leg 813 so that top surface 870-3 extends from and curves around curved end 413-2 to leg 813. The height and horizontal extent of drape guide lip 870 is selected so that when surgical drape 360 is cinched to links 419 and 413, any excess sterile drape material cannot contact the non-sterile drape material above drape guide lip 870 as link 419 moves under link 413.

Figure 11:
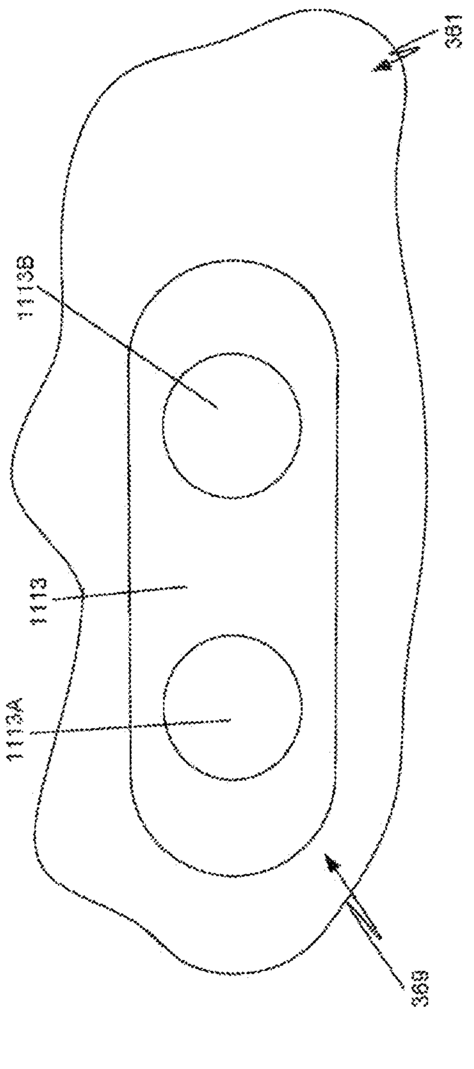
FIG. 11 is an illustration of an alignment and attachment element.

FIG. 11 is an illustration of an alignment and attachment element assembly 369, which is attached to first portion 361 of surgical drape 360. Alignment and attachment element assembly 369 includes a support member 1113 that is affixed to the inner side of surgical drape 360—e.g., a first side of support member 1113 is affixed to the inner side of surgical drape 360.

To position support member 1113 at the proper location on the inner surface of the surgical drape, a template is used and support member 1113 is affixed to surgical drape 360 using double-sided pressure-sensitive tape. In one aspect, support member 1113 is made from a high strength, moderate stiffness material, e.g., high density polyethylene (HDPE), but other materials can be used, as previously described.

A pair of attachment elements 1113A and 1113B is affixed, by using double-sided pressure-sensitive tape, to a side of support member 1113 (a second side) opposite to the first side of support member 1113 that is affixed to surgical drape 360. Attachment elements 1113A and 1113B are separated on support member 1113 by the same distance as the distance between alignment receptacles 413A and 413B.

Attachment element 1113A fits in attachment receptacle 413A, and attachment element 1113B fits in attachment receptacle 413B, to secure first drape portion 361 to first end 413-1 of first link 413 and to properly position the open end of first drape portion 361 on first link 413. In one aspect, attachment receptacles 413A and 413B are magnetized, and attachment element 1113A and 1113B are metal discs that are held in attachment receptacles 413A and 413B, respectively, by the magnetism.

As used herein, “first”, “second”, “third”, etc. are adjectives used to distinguish between different components or elements. Thus, “first”, “second”, and “third” are not intended to imply any ordering of the components or elements, or to imply any total number of components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description’s terminology is not intended to limit the invention. For example, spatially relative terms-such as “beneath”, “below”, “lower”, “above”, “upper”, “proximal”, “distal”, and the like—may be used to describe one element’s or feature’s relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as “below” or “beneath” other elements or features would then be “above” or “over” the other elements or features. Thus, the exemplary term “below” can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms “a”, “an”, and “the” are intended to include the plural forms as well, unless the context indicates otherwise. The terms “comprises”, “comprising”, “includes”, and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

Embodiments described above illustrate but do not limit the disclosure. It should also be understood that numerous modifications and variations are possible in accordance with the principles of the present disclosure. For example, in many aspects the devices described herein are used as single-port devices; i.e., all components necessary to complete a surgical procedure enter the body via a single entry port. In some aspects, however, multiple devices and ports may be used.

What is claimed is:

1. A sterile drape assembly for a surgical system, comprising:
- a sterile drape; and
- a cinch assembly affixed to the sterile drape, the cinch assembly comprising at least two of:
  - a hinged cinch assembly comprising a pair of links connected by a hinge joint, wherein:
    - the hinge joint is a scored region of material between the pair of links,
    - each link of the pair of links is foldable relative to one another about the hinge joint between an unfolded configuration and a folded configuration,
    - wherein a portion of the sterile drape is in an extended configuration in the unfolded configuration of the pair of links and is in a gathered configuration in the folded configuration of the pair of links, and
    - wherein, in the unfolded configuration, the pair of links define an elongate dimension and the scored region extends perpendicular to the elongate dimension;
  - an alignment and attachment assembly comprising a first attachment element and a second attachment element, wherein the first and second attachment elements are configured to align with and engage with respective first and second complementary attachment elements of equipment of a surgical system; or
  - an attachment assembly comprising another pair of links with a third attachment element mounted on one link of the another pair of links, wherein the third attachment element is configured to engage with a third complementary attachment element of equipment of a surgical system.

2. The sterile drape assembly of claim 1, wherein the attachment assembly further comprises a second cinch assembly affixed to the sterile drape, wherein the second cinch assembly comprises a plurality of links connected by an additional hinge joint.

3. The sterile drape assembly of claim 2, wherein the additional hinge joint comprises a living hinge.

4. The sterile drape assembly of claim 1, wherein the first and second attachment elements are configured to engage with the first and second complementary attachment elements of an active manipulator link of a manipulator system of a surgical system.

5. The sterile drape assembly of claim 4, wherein the third attachment element is configured to engage with a third complementary attachment assembly located at an opposite end of the active manipulator link from the first and second complementary attachment elements.

6. The sterile drape assembly of claim 1, wherein the hinged cinch assembly further comprises:

a first connector component mounted on a first link of the pair of links; and a second connector component mounted on a second link of the pair of links, wherein the first and second connector components are configured to mate together to be placed in a mated state, and wherein in a state of the first and second connector components mated together, the pair of links is in the folded configuration.

7. The sterile drape assembly of claim 6, wherein the first and second connector components comprise a hook and loop fastening mechanism.

8. The sterile drape assembly of claim 1, wherein the hinged joint comprises a living hinge.

9. The sterile drape assembly of claim 1, wherein the first, second, and third attachment elements are configured to attach with the first, second, and third complementary attachment elements by magnetic force.

10. The sterile drape assembly of claim 1, wherein the hinged cinch assembly is configured to gather and cinch the portion of the sterile drape around an entry guide manipulator portion of a manipulator system of a surgical system.

11. The sterile drape assembly of claim 1, wherein the pair of links of the hinged cinch assembly is a first pair of links and wherein the portion of the sterile drape is a first portion of the drape, wherein the hinged cinch assembly further comprises a second pair of links and at least one additional hinge joint connecting adjacent links of the second pair of links, wherein the second pair of links are foldable relative to one another about the at least one additional hinge joint between an unfolded configuration and a folded configuration, and wherein a second portion of the sterile drape is in an extended configuration in the unfolded configuration of the second pair of links and is in a gathered configuration in the folded configuration of the second pair of links.

12. The sterile drape assembly of claim 1, wherein the cinch assembly comprises each of the hinged cinch assembly, the alignment and attachment assembly, and the attachment assembly.

13. The sterile drape assembly of claim 1, wherein the cinch assembly is affixed to the sterile drape via pressure-sensitive adhesive.

14. The sterile drape assembly of claim 1, wherein the cinch assembly is made of high density polyethylene.

15. The sterile drape assembly of claim 1, wherein manipulation of the pair of links from the unfolded configuration to the folded configuration creates a fold in the sterile drape.

* * * * *